United States Patent [19]

Az et al.

[11] Patent Number: 5,240,499

[45] Date of Patent: Aug. 31, 1993

[54] SURFACTANT TRIAZINE COMPOUNDS AND THEIR USE

[75] Inventors: Rainer Az, Hofheim am Taunus; Wolfgang Schwab, Kelsterbach; Dieter Schnaitmann, Eppstein/Taunus; Erwin Dietz, Kelkheim, all of Fed. Rep. of Germany

[73] Assignee: Hoechst Aktiengesellschaft, Frankfurt, Fed. Rep. of Germany

[21] Appl. No.: 808,520

[22] Filed: Dec. 13, 1991

[30] Foreign Application Priority Data

Dec. 21, 1990 [DE] Fed. Rep. of Germany ....... 4041215

[51] Int. Cl.$^5$ .................. A01N 43/66; C07D 251/26; C07D 251/40
[52] U.S. Cl. .............................. 106/498; 252/301.21; 252/357; 504/227; 544/194; 544/195; 544/196; 544/198; 544/204; 544/209; 544/212; 544/214
[58] Field of Search ............... 544/198, 206, 207, 208, 544/209, 212, 219, 214, 194, 195; 252/357, 301.21; 106/498

[56] References Cited

U.S. PATENT DOCUMENTS

| | | | |
|---|---|---|---|
| 2,394,306 | 2/1946 | Hentrich et al. | 544/210 |
| 3,622,339 | 11/1971 | Nishio et al. | 96/109 |
| 4,189,582 | 2/1980 | Hoch et al. | 546/37 |
| 4,228,281 | 10/1980 | Kainmüller et al. | 544/198 |
| 4,253,839 | 3/1981 | Spietschka et al. | 8/565 |
| 4,281,110 | 7/1981 | Kainmüller et al. | 528/289 |
| 4,314,001 | 2/1982 | Wesseler | 428/393 |
| 4,347,352 | 8/1982 | Wesseler | 528/423 |
| 4,496,731 | 1/1985 | Spietschka et al. | 546/37 |

FOREIGN PATENT DOCUMENTS

| | | | |
|---|---|---|---|
| 0088392 | 9/1983 | European Pat. Off. | 5/62 |
| 1772815 | 10/1970 | Fed. Rep. of Germany | 1/34 |
| 2742575 | 9/1977 | Fed. Rep. of Germany | 67/00 |
| 2727484 | 1/1979 | Fed. Rep. of Germany | 3/18 |
| 2840960 | 4/1979 | Fed. Rep. of Germany | 251/70 |

Primary Examiner—Mukund J. Shah
Assistant Examiner—Y. N. Gupta
Attorney, Agent, or Firm—Connolly and Hutz

[57] ABSTRACT

Polymeric, water-soluble triazine compounds which contain both basic and acidic groups in the molecule have out-standing surfactant properties and are suitable for the preparation of dispersions of solids, preferably of dispersions of inorganic and/or organic pigments, in an aqueous or water-dilutable medium. Since these triazine compounds are colorless or only slightly colored, they do not influence the shade of the medium used.

5 Claims, No Drawings

SURFACTANT TRIAZINE COMPOUNDS AND THEIR USE

The present invention relates to the technical area of the surfactant compounds.

The triazine compounds mainly used at present in industry are crop protection agents, melamine resins and especially textile dyes. Such compounds are, as a rule, composed of a triazine ring, sometimes two triazine rings, which are substituted by chromophores. In general, these dyes are rendered water-soluble by substituents on the chromophores. To influence the tinctorial properties, the triazine ring may carry further substituents, for example amino groups having aliphatic radicals, vinylsulfonyl groups and alkoxy groups. Such compounds are used for dyeing textile materials. Oligomeric and polymeric triazine compounds which are composed of more than two triazine rings are also known. U.S. Pat. No. 4,314,001 and U.S. Pat. No. 4,347,352 describe polymeric triazine compounds of the general formula I (see formulae), in which Y and Z are substituents containing amino groups, which compounds are suitable as mordants for water-soluble dyes on cellulose, as fixing agents for pigments on cellulose or as surfactants for aqueous pigment dispersions. U.S. Pat. No. 3,622,339 likewise mentions polymeric triazine compounds of the general formula II (see formulae), in which $R^1$ is a radical containing amino, hydroxyalkyl or mercapto groups, $R^2$, $R^3$, $R^4$ and $R^5$ are each hydrogen or an alkyl group and $Y^1$ and $Y^2$ are each an unsubstituted or substituted alkylene or arylene diradical, which compounds are used as antifogging agents in film emulsions. U.S. Pat. No. 4,228,281 describes dicarboxylic acids which contain polymeric triazine rings and are of the general formula III (see formulae), in which $R^1$, $R^2$, $R^3$ and $R^5$ are each hydrogen or a $C_1$–$C_{22}$-alkyl hydrocarbon radical, $R^4$ is a $C_2$–$C_{18}$-hydrocarbon diradical and $R^6$ is a $C_1$–$C_{12}$-hydrocarbon diradical, which acids are used for the synthesis of polyesters having a glass transition temperature above 100° C.

It is the object of the present invention to provide polymeric water-soluble triazine compounds which are colorless or only slightly colored, have good surfactant properties and may also be suitable for pigmenting or for coating the surface of pigments. The object is achieved by a novel class of triazine compounds which contain basic and acidic groups and are of the general formula IV (see formulae), in which X is a group of the formula IVa (see formulae), in which $A^1$ is a bridge member selected from the group comprising O, S or $NR^3$, wherein $R^3$ is hydrogen or a $C_1$–$C_{22}$ -alkyl radical or a $C_3$–$C_{22}$-alkenyl radical, preferably a $C_1$–$C_4$-alkyl radical or hydrogen, in particular methyl or hydrogen, which is unsubstituted or substituted by an OH group, $D^1$ is an arylene group or a branched or straight-chain $C_2$–$C_{12}$ -alkylene group, which may be interrupted by one or more bridge members selected from the group $A^2$, and $A^2$, independently of $A^1$, is selected from the same group of substituents as $A^1$, and $R^1$ and $R^2$, independently of one another, are branched or straight-chain $C_1$–$C_{20}$ -alkyl groups or $C_2$–$C_{20}$-alkenyl groups, preferably $C_1$–$C_6$-alkyl groups, or in which $R^1$ and $R^2$, together with the nitrogen atom, form an unsaturated or saturated five- or six-membered ring which may additionally contain one or two nitrogen, oxygen and/or sulfur atoms as further hetero atoms in the ring, or in which X is a group of the formula IVb (see formulae), wherein $R^4$ is $C_1$–$C_6$-alkyl and $Y^1$ and $Y^2$, independently of one another are each a group of the formula IVc (see formulae), in which $A^3$ is independent of $A^1$ and is a bridge member selected from the same group of substituents as $A^1$, $D^2$ is independent of $D^1$ and is selected from the same group of substituents as $D^1$ or is $CH_2$ or a direct bond, and $E^1$ is an anion-forming group, preferably COOM, $SO_3M$, $OSO_3M$ or $OPO_3M_2$, in which M is hydrogen, a metal, in particular an alkali metal or the stoichiometric amount of an alkaline earth metal, or an ammonium ion which is unsubstituted or substituted by aliphatic, aromatic and araliphatic radicals, and Z is a group of the formula IVd (see formulae), in which $A^4$ is independent of $A^1$ and is a bridge member selected from the same group of substituents as $A^1$ and $Z^*$ is the group CO, branched or straight-chain $C_2$–$C_{25}$-alkylene, $C_5$–$C_6$-cycloalkylene or $C_6$–$C_{14}$-arylene, preferably $C_2$–$C_6$-alkylene or phenylene, which is unsubstituted or substituted by COOM, $SO_3M$, Cl, OH or alkoxy groups, wherein M has the abovementioned meanings and wherein, in the cyclic compounds, some of the carbon atoms may be replaced by the hetero atoms nitrogen, oxygen and/or sulfur, or wherein Z is a bridge member of the general formulae IVe and IVf (see formulae), in which $A^5$ is a group of the formula $CR^5R^6$, $NR^7$, O, SO, $SO_2$ or CO, preferably $CR^5R^6$, $NR^7$ or O, in which $R^5$ and $R^6$, independently of one another, may be branched or straight-chain $C_1$–$C_4$ -alkyl groups or hydrogen, and in which $R^7$, independently of $R^3$, is selected from the same group of substituents as $R^3$, or Z is any combination of groups of the formulae IVd, IVe and/or IVf, and m is an integer of from 1 to 100.

Preferred compounds of the general formula IV (see formulae) are those in which X is a group of the formula IVa (see formulae), in which $A^1$ is a bridge member selected from the group comprising O and $NR^3$, in which $R^3$ is hydrogen or a $C_1$–$C_{22}$-alkyl radical or a $C_3$–$C_{22}$ -alkenyl radical, preferably a $C_1$–$C_4$-alkyl radical or hydrogen, in particular methyl or hydrogen, which is unsubstituted or substituted by an OH group, $D^1$ is an arylene group or a branched or straight-chain $C_2$–$C_{12}$-alkylene group which may be interrupted by one or more bridge members selected from the group $A^2$, and $A^2$, independently of $A^1$, is selected from the same group of substituents as $A^1$, and $R^1$ and $R^2$, independently of one another are branched or straight-chain $C_1$–$C_{20}$ -alkyl groups or $C_3$–$C_{20}$-alkenyl groups, preferably $C_1$–$C_6$-alkyl groups, or in which $R^1$ and $R^2$, together with the nitrogen atom, form an unsaturated or saturated five- or six-membered ring which may additionally contain one or two nitrogen or oxygen atoms as further hetero atoms in the ring, or in which X is a group of the formula IVb (see formulae), wherein $R^4$ is $C_1$–$C_6$-alkyl, and $Y^1$ and $Y^2$, independently of one another are each a group of the formula IVc (see formulae), in which $A^3$ is independent of $A^1$ and is a bridge member selected from the same group of substituents as $A^1$, $D^2$ is independent of $D^1$ and is selected from the same group of substituents as $D^1$, or is $CH_2$ or a direct bond, and $E^1$ is an anion-forming group, preferably COOM or $SO_3M$, wherein M is hydrogen, a metal, in particular an alkali metal or the stoichiometric amount of an alkaline earth metal, or an ammonium ion, which is unsubstituted or substituted by aliphatic, aromatic or araliphatic radicals, and Z is a group of the formula IVd (see formulae), in which $A^4$ is independent of $A^1$ and is a bridge member selected from the same group of substituents as $A^1$, and $Z^*$ is the group CO, $NR^3$, in which $R^3$ has the abovementioned meaning, branched or straight-chain $C_2$-$C_{25}$-alkylene, $C_5$-$C_6$-cycloalkylene or phenylene, preferably $C_2$-$C_6$-alkylene or phenylene, which is unsubstituted or substituted by COOM or $SO_3M$, in which M has the abovementioned meanings, and wherein, in the cyclic compounds, some of the carbon atoms may be replaced by the hetero atoms nitrogen and/or oxygen, or Z is a combination of the groups of the formula IVd, and m is an integer of from 1 to 100.

Particularly preferred compounds of the general formula IV (see formulae) are those in which X is a group of the formula IVg (see formulae), in which $R^8$ is methyl or hydrogen, and $D^1$ is a branched or straight-chain $C_2$-$C_6$-alkylene group or a phenylene group, and $R^1$ and $R^2$ are independently of one another branched or straight-chain $C_1$-$C_6$-alkyl groups, or in which $R^1$ and $R^2$, together with the nitrogen atom, form an unsaturated or saturated five-or six-membered ring which may additionally contain one or two nitrogen and/or oxygen atoms as further hetero atoms in the ring, and $Y^1$ and $Y^2$, independently of one another are each a group of the formula IVh (see formulae), in which $R^9$ is independent of $R^8$ and is a substituent selected from the same group as $R^8$, and $D^2$ is independent of $D^1$ and is selected from the same group of substituents as $D^1$ or is $CH_2$ or a direct bond, and $E^1$ is an anion-forming group, preferably COOM or $SO_3M$, wherein M is hydrogen, a metal, in particular an alkali metal or the stoichiometric amount of an alkaline earth metal, or an ammonium ion, which is unsubstituted or substituted by aliphatic, aromatic and araliphatic radicals, and Z is a group of the formula IVi (see formulae), in which $R^{10}$ is methyl or hydrogen, and $Z^*$ is the group $C_2$-$C_6$-alkylene or phenylene, which is unsubstituted or substituted by COOM or $SO_3M$, wherein M has the abovementioned meanings, or in which $Z^*$ is a group of the formula IVj (see formulae), in which $Z^{**}$ is the group N-$C_1$-$C_{20}$-alkyl, NH or O, and m is an integer of from 1 to 30.

The compounds according to the invention are colorless or only slightly colored, which enables them to be used widely in the area of surfactant substances, since they do not influence the shade of the medium in which they are used.

According to the prior art, triazine compounds are synthesized by a nucleophilic substitution of the halogen atoms in cyanuric halides, in particular cyanuric chloride, by amine, hydroxy or mercapto derivatives at temperatures of $-10°$ to $+200°$ C. (J. Am. Chem. Soc. Vol. 73 (1951), 2981-2996). The substitution reaction can be selectively controlled by temperature control and pH monitoring, which is carried out by means of acid acceptors, such as, for example, sodium hydroxide solution or sodium carbonate. Substitution of all three halogen atoms with different radicals can be carried out in succession in a single reaction vessel. However, this process is not applicable to the compounds according to the invention, since $Y^1$ and $Y^2$ can be introduced only with the random distribution thereby. If the reactivities of $Y^1$-H and $Y^2$-H differ greatly from one another, it is possible that only $Y^1$ or $Y^2$ is substitutable. The products of the general formula IV in which $Y^1 = Y^2$, which are formed in the synthesis in a single reaction vessel, possess physical and chemical properties which are not very suitable for the intended application.

The present invention furthermore relates to a process for the synthesis of a compound of the general formula IV, wherein, in separate containers, first a compound of the formula $Y^1$-H (first reaction batch) and one of the formula $Y^2$-H (second reaction batch) are each reacted in aqueous solution with a cyanuric halide, preferably cyanuric chloride, at a temperature of 0° to 10° C., preferably 0° to 5° C., then the intermediate formed in the reaction batch is reacted with a compound of the formula X-H and the intermediate formed in the second reaction batch is reacted with a compound of the formula $ZH_2$, in each case at a temperature of from 20° to 60° C., preferably 35° to 45° C., and the two reaction batches are then combined and are reacted with 0.1 to 0.6 mol of $ZH_2$ per mol of cyanuric halide used, at a temperature of 70° to 150° C., preferably 75° to 95° C.

As a result of this reaction procedure, the two terminal triazine rings each contain the acidic group $Y^1$ and the substituent X having a basic function, in particular a tertiary nitrogen atom, while all other triazine rings are substituted by the acidic group $Y^2$. The synthesis is carried out in two separate reaction vessels, the reaction preferably being carried out in water as a solvent, to which small amounts of a surfactant, for example a sulfonated fatty acid derivative, have been added.

In the first step, the groups $Y^1$ or $Y^2$ are bonded to the cyanuric halide in water in separate stirred vessels (A) and (B). For this purpose, 0.8 to 1.2 mol of $Y^1$-H or $Y^2$-H are used per mol of cyanuric halide, and the reaction is carried out at 0° to 10° C., preferably 0° to 5° C. In an idealized form, the reactions take place according to reaction scheme 1 (see formulae).

In the second step, the group X in reaction vessel (A) (reaction product V) on the one hand and the group Z in reaction vessel (B) (reaction product VI) on the other hand are substituted at 20° to 60° C., preferably 35° to 45° C. (reaction scheme 2, see formulae). In this step, 0.8 to 1.2 mol of X-H or 0.3 to 1.2 mol of H-Z-H are used in each case per mol of cyanuric halide. Thereafter, the two resulting intermediates VII and VIII are bonded via Z at 70° to 150° C., preferably 75° to 95° C., 0.1 to 0.6 mol of H-Z-H being used per mol of cyanuric halide (reaction scheme 3, see formulae). This amount of H-Z-H may advantageously also be present in the reaction of VI to give VIII.

To neutralize the acid HHal formed in the reaction, an acid acceptor, for example sodium hydroxide solution or potassium hydroxide solution, sodium carbonate, sodium bicarbonate or potassium carbonate, is added in each reaction stage, gradually as the reaction progresses (decrease in pH) or all at once, in an amount such that the pH of the reaction mixtures is 6 to 9. The reaction mixture obtained in this manner can be used directly for the applications according to the invention, if necessary after any solid constituents present have been filtered off. Furthermore, the reaction product can be precipitated from the solution by adding acids, for example hydrochloric acid or sulfuric acid, and separated off by filtration. The solvent can be removed from the reaction mixture by means of a vacuum, elevated temperature or spray drying, and the resulting salt can be removed by adding organic solvents, preferably dimethyl sulfoxide. The salt can also be separated off by membrane separation methods.

After precipitation by means of an acid, the product can be used as a surfactant in the form of the still moist press cake, in a dry form and in the form of an amine, alkali metal salt or alkaline earth metal salt solution. Examples of amines for salt formation are: methylamine, mono-, di- and triethylamine, mono-, di- and triethanolamine, dimethylethanolamine, methyldiethanolamine and dimethylaminomethylpropanol.

Examples of the compounds of the formula X-H are N,N-dimethyl-p-phenylenediamine, N,N-diethyl-p-phenylenediamine, aminobenzyldimethylamine, 2-dimethylaminoethylamine, 3-diethylaminopropylamine, 3-dimethylaminopropylamine, $N^1,N^1$-diethyl-1,4-pentanediamine, N,N-dimethylneopentanediamine, 2-pyrrolidinoethylamine, N-(3-aminopropyl)-imidazole, dimethylneopentanolamine or 4-dimethylamino-1-butanol.

Examples of the compounds of the formulae $Y^1$-H and $Y^2$-H are o-, m- and p-aminobenzoic acid, o-, m- and p-aminobenzenesulfonic acid, glycine, alanine, β-alanine, 4-aminobutyric acid, amidosulfonic acid, 2-aminoethanesulfonic acid, o-, m- and p-hydroxybenzoic acid, phenolsulfonic acid, 6-hydroxycaproic acid, 5-hydroxyvaleric acid, 4-hydroxybutyric acid, 4-hydroxy-1-butanesulfonic acid, hydroxynaphthalenesulfonic acid, hydroxypivalic acid or mercaptoacetic acid.

Examples of the compounds of the formulae $ZH_2$ are 1,2-diaminoethane, 1,2-diaminopropane, 1,3-diaminopropane, 1,4-diaminobutane, 1,6-diaminohexane, 1,8-diaminooctane, 1,12-diaminododecane,neopentanediamine,3,6-dioxaoctane-1,8-diamine, 4,7-dioxadecane-1,10-diamine, 4,9-dioxadodecane-1,12-diamine, 4,7,10-trioxadodecane-1,12-diamine, 4,7,10-trioxatridecane-1,13-diamine, 4,4'-diaminodicyclohexylmethane, 4,4'-diaminodiphenylmethane, N-(2-aminoethyl)-1,2-ethanediamine, N-(2-aminopropyl)-1,3-propanediamine, 4,4'-diaminodiphenyl ether, 4-amino-N-(4-aminophenyl)-benzenesulfonamide, 4,4'-diaminobenzanilide, 1,4-phenylenediamine-2-sulfonic acid, 4,4'-dihydroxydiphenyl sulfone or o-, m- and p-dihydroxybenzene.

The compounds according to the invention of the general formula IV are in the protonated form, in the form of the zwitter ion or in the deprotonated form, depending on the pH.

The compounds according to the invention are in general readily soluble in polar and in protic solvents, if necessary at elevated pH. The surfactant properties of the compounds according to the invention are evident, for example, in the reduction of the surface tension of an aqueous solution. This can be determined by the ring tear method (DIN 53,914) and, depending on the compound, gives values of 35 to 45 mN/m at a measurement temperature of 25° C. in aqueous amine-alkaline solution (pH 9.0) (comparative value of an aqueous amine-alkaline solution at pH 9.0:70 mN/m).

The compounds according to the invention are suitable as dispersants, emulsifiers and distributing agents for solids in aqueous media. The present invention therefore also relates to the use of the compounds according to the invention as surfactants and as dispersants, emulsifiers or distributing agents for solids in aqueous media. In particular, the compounds according to the invention can be used in dispersions which contain, as solids, for example minerals, crop protection agents and pesticides, dyes, pigments and optical brighteners. Furthermore, the compounds according to the invention are suitable as dyeing assistants and stabilizers, for the wet-end coloring of regenerated cellulose and as dispersants for aqueous flexographic printing. The suitability of the compounds according to the invention for the production of highly pigmented, free-flowing pigment preparations of inorganic and organic pigments, such as, for example, azo pigments, quinacridones, flavanthrone, anthanthrone and pyranthrone pigments, derivatives of naphthalenetetracarboxylic acid and of perylenetetracarboxylic acid, of thioindigo, of dioxazine, of the isoindolines, of the isoindolinones and of the diketopyrrolopyrroles, laked pigments, such as the magnesium, calcium, strontium, barium, aluminum, manganese and nickel lakes of dyes containing acid groups, of phthalocyanine pigments and of corresponding pigment mixtures must be particularly emphasized. The abovementioned pigment preparations are understood as meaning on the one hand pigment dispersions in concentrated form which can be converted into the final lake formulation by dilution with binders based on aqueous polyacrylate, polyester and polyurethane systems and on the other hand pigment preparations which are incorporated in powder form into the medium used.

The invention thus relates to pigment dispersions essentially containing at least one of the compounds of the formula IV and at least one inorganic and/or organic, preferably polycyclic, pigment. The invention furthermore relates to pigment preparations of organic, preferably polycyclic, pigments, in particular of perylene and dioxazine pigments and of quinacridones. The compounds according to the invention, of the formula IV, can be used individually or as a mixture and also in combination with other nonionic, anionic or cationic surfactants or mixtures thereof. They can also be used together with builders or other conventional additives or assistants. The composition of the stated pigment preparations can vary within wide limits.

The preferred pigment preparation essentially consists of
a) 99.5 to 50% by weight, preferably 97 to 70% by weight, of at least one organic, preferably polycyclic, pigment,
b) 0.5 to 30% by weight, preferably 3 to 20% by weight, of at least one compound of the formula IV and
c) 0 to 20% by weight, preferably 0 to 10% by weight, of further conventional additives, for example foam regulators and viscosity regulators, surfactants, sedimentation inhibitors, wetting agents and preservatives.

The present invention also relates to a process for the preparation of the pigment preparations, wherein the surface of the pigments is coated with at least one of the compounds of the formula IV. Depending on the embodiment, application of these compounds to the pigment particles may be effected either in aqueous suspension, in organic solvents or in mixtures of water or organic solvents. There are a number of possibilities for applying the compounds according to the invention to the pigment surface. This may be carried out during or after the pigment synthesis or during or after a finish process. Compounds of the formula IV can also be added during incorporation of the pigments into the medium used. When the compounds according to the invention are applied to the pigment surface in aqueous suspension or in water/solvent mixtures, the pigment is then usually isolated by filtration. As a rule, the pH has an effect on the pigment properties. A pH of 7 to 12, particularly preferably 7.5 to 9, is preferred.

The invention also relates to the use of the pigment dispersions and pigment preparations according to the invention for pigmenting and coloring natural and synthetic materials. A preferred use is for the preparation of aqueous coatings, emulsion paints and printing inks. The use of the pigment preparations and of the pigment dispersions for pigmenting aqueous coating systems is particularly preferred. In all conventional aqueous binder systems, such as polyacrylates, polyurethanes and polyesters, the pigment preparations and pigment dispersions according to the invention give pure brilliant shades with high color strength and high transparency. The pigment pastes have good rheological properties in conjunction with high pigment contents and constant pH, even after storage at elevated temperatures for several weeks. For testing the suitability, the compounds described in the Examples below are either applied to the pigments or are used for dispersing pigments in aqueous coating systems. The coating systems chosen are aqueous polyacrylate, polyester and polyurethane systems. The performance characteristics (color strength, shade, transparency) of the baking enamels produced with these coatings are tested. To evaluate the coloristic criteria, the dilute full shade coatings are applied either with a hand coater (coil coater, 24 μm wet film thickness) to transparent polyester film or with a film coater (coil film coater, 15 μm wet film thickness) to contrast cardboard. The rheology was assessed visually on the basis of the stock pastes after dispersion.

The following five-stage scale was used as a basis:
5: low viscosity
4: fluid
3: viscous
2: slightly set
1: completely set After dilution of the mill base to the final pigment concentration, the viscosity (visc) can be determined using a Rossmann visco-spatula, Type 301 from Erichsen, Iserlohn. Before the coating process, the desired viscosity was set so that it corresponded to a certain efflux time in the Ford cup (nozzle of 4 mm diameter), stated in seconds (s).

The color strength and shade were evaluated on the basis of white reductions with $TiO_2$ or of metallic blends with aluminum.

The coloristic evaluation was carried out on the basis of the 6-stage evaluation scale stated below:
1: very little
2: slight
3: marked
4: distinct
5: significant
6: considerable The gloss measurements were carried out at an angle of 20° according to DIN 67,530 (ASTMD 523) using a "multi-gloss" gloss meter from Byk-Mallinckrodt, Wesel. The gloss values stated in the Examples are dimensionless reflectance values. In the Preparation and Use Examples below, parts relate to parts by weight and percentages are percentages by weight. The abbreviations used have the following meanings:

"FS 3% P" means "Full shade 3% pigment content".

"1:10 $TiO_2$" means "Mixture of 1 part of colored pigment and 10 parts of titanium dioxide white pigment".

"50:50 Met" means "Mixture of 50 parts of colored pigment and 50 parts of aluminum pigment".

"D water" means "Demineralized water".

SYNTHESIS EXAMPLES

1) For the synthesis of the compound of formula IV in which $X = -NH-CH_2-CH_2-CH_2-N(C_2H_5)_2$, $Y^1 = Y^2 = -NH-C_6H_4-SO_3H$, $Z = -NH-CH_2-CH_2-NH-$ and m=2, 17.3 parts of sulfanilic acid were added to 400 parts of a water/ice mixture which contained 0.2 part of a sulfonated fatty acid derivative and 18.5 parts of cyanuric chloride, in stirred vessel (A), at 0° to 5° C., and the pH was kept at 6 to 9 by adding 0.2 normal NaOH solution. After the addition of the alkali, stirring was continued for about one hour at 0° to 5° C. Thereafter, 13.0 parts of diethylaminopropylamine were added at about 40° C. and the pH was kept at 6 to 9 by adding 0.2 normal NaOH solution. After the addition of the alkali, stirring was continued for about one hour at about 40° C. In stirred vessel (B), 17.3 parts of sulfanilic acid were added to 400 parts of a water/ice mixture which contained 0.2 part of a sulfonated fatty acid derivative and 18.5 parts of cyanuric chloride, at 0° to 5° C., and the pH was kept at 6 to 9 by adding 0.2 normal NaOH solution. After the addition of the alkali, stirring was continued for about one hour at 0° to 5° C. Thereafter, 3.0 parts of diaminoethane were added at about 40° C., and the pH was kept at 6 to 9 by adding 0.2 normal NaOH solution. After the addition of the alkali, stirring was continued for about one hour at 40° C. The content of the stirred vessel (B) was then added to stirred vessel (A), and 6.0 parts of diaminoethane were added at 80° C. and the pH was kept at 6 to 9 by adding 0.2 normal NaOH solution. After the addition of the alkali, stirring was continued for about a further five hours at 95° C. After the reaction mixture had cooled at room temperature, the pH was adjusted to 1.5 with concentrated hydrochloric acid and the precipitate formed was filtered off and dried.

IR (KBr, $cm^{-1}$) 3300, 3100, 1630, 1590, 1550, 1500, 1220, 1170, 1030, 1000

2) For the synthesis of the compound of the formula IV in which $X = -NH-CH_2-CH_2-CH_2-$imidazolyl, $Y^1 = -NH-CH_2-CH_2-SO_3H$, $Y^2 = -NH-CH_2-CH_2-COOH$, $Z = -NH-C_6H_4-NH-$ and m=2, 25.0 parts of taurine were added to 400 parts of water/ice mixture which contained 0.4 part of a sulfonated fatty acid derivative and 36.9 parts of cyanuric chloride, in stirred vessel (A) at 0° to 5° C., and the pH was kept at 6 to 9 by adding 0.2 normal NaOH solution. After the addition of the alkali, stirring was continued for about one hour at 0° to 5° C. Thereafter, 25.0 parts of N-(3-aminopropyl)-imidazole, dissolved in 50 parts of water, were added at about 40° C. and the pH was kept at 6 to 9 by adding 0.2 normal NaOH solution. After the addition of the alkali, stirring was continued for about one hour. In stirring vessel (B), 17.8 parts of β-alanine, dissolved in 100 parts of water, were added to 400 parts of a water/ice mixture which contained 0.4 part of a sulfonated fatty acid derivative and 36.9 parts of cyanuric chloride, at 0° to 5° C., and the pH was kept at 6 to 9 by adding 0.2 normal NaOH solution. After the addition of the alkali, stirring was continued for about one hour at 0° to 5° C. Thereafter, 32.4 parts of p-phenylenediamine were added at about 40° C. and the pH was kept at 6 to 9 by adding 0.2 normal NaOH solution. After the addition of the alkali, stirring was continued for about one hour at about 40° C.

The content of the stirred vessel (B) was then added to stirred vessel (A) and, at about 80° C., the pH was kept at 6 to 9 by adding 0.2 normal NaOH solution. After the addition of the alkali, stirring was continued for about a further five hours at about 95° C. After the reaction mixture had cooled to room temperature, the pH was adjusted to 1.5 with concentrated hydrochloric acid and the precipitate formed was filtered off and dried.

IR (KBr, cm$^{-1}$) 3300, 3100, 1630, 1570, 1500, 1410, 1220, 1160, 1030

EXAMPLES 3–8

The following compounds of the formula IV having the substituents X, $Y^1$, $Y^2$ and Z were reacted according to Examples 1 and 2:

| No. | X | $Y^1$, $Y^2$ each | Z | m |
|---|---|---|---|---|
| 3 | —NH—(CH$_2$)$_3$—N(C$_2$H$_5$)$_2$ | —NH—C$_6$H$_4$—SO$_3$H | —NH—C$_6$H$_4$—NH— | 2 |
| 4 | —NH—(CH$_2$)$_3$—N(C$_2$H$_5$)$_2$ | —NH—C$_6$H$_4$—SO$_3$H | —NH—C$_6$H$_4$—NH— | 5 |
| 5 | —NH—(CH$_2$)$_3$—CH(CH$_3$)N(C$_2$H$_5$)$_2$ | —NH—CH$_2$CH$_2$—SO$_3$H | —NH—C$_6$H$_4$—NH— | 5 |
| 6 | —NH—(CH$_2$)$_3$—N(C$_2$H$_5$)$_2$ | —NH—CH$_2$—CH$_2$—SO$_3$H | —NH—C$_6$H$_4$—NH— | 2 |
| 7 | —NH—(CH$_2$)$_3$—N(C$_2$H$_5$)$_2$ | —NH—CH$_2$—CH$_2$—SO$_3$H | —NH—C$_6$H$_4$—NH— | 2 |
| 8 | —NH—(CH$_2$)$_3$-imidazolyl | —NH—C$_6$H$_4$—COOH | —NH—C$_6$H$_4$—NH— | 2 |

| | Amounts of educts: (p = parts) | | | | |
|---|---|---|---|---|---|
| No. | Stirred vessel (A) at 0 to 5° C. | Stirred vessel (A) at 40° C. | Stirred vessel (B) at 0 to 5° C. | Stirred vessel (B) at 40° C. | at 80° C. |
| 3 | 18.5 p. of cyanuric chloride 17.3 p. of sulfanilic acid | 13.0 p. of diethylaminopropylamine | 18.5 p. of cyanuric chloride 17.3 p. of sulfanilic acid | 5.4 p. of p-phenylenediamine | 10.8 p. of p-phenylenediamine |
| 4 | 11.1 p. of cyanuric chloride 10.4 p. of sulfanilic acid | 7.8 p. of diethylaminopropylamine | 27.7 p. of cyanuric chloride 26.0 p. of sulfanilic acid | 6.5 p. of p-phenylenediamine | 13.0 p. of p-phenylenediamine |
| 5 | 18.5 p. of cyanuric chloride 12.5 p. of taurine | 15.8 p. of N,N-diethylamino-4-aminopentane | 46.1 p. of cyanuric chloride 31.3 p. of taurine | 21.6 p. of p-phenylenediamine | 10.8 p. of p-phenylenediamine |
| 6 | 20.3 p. of cyanuric chloride 12.5 p. of taurine | 13.0 p. of diethylaminopropylamine | 20.3 p. of cyanuric chloride 12.5 p. of taurine | 5.4 p. of p-phenylenediamine | 10.8 p. of p-phenylenediamine |
| 7 | 18.5 p. of cyanuric chloride 12.5 p. of taurine | 13.0 p. of diethylaminopropylamine | 18.5 p. of cyanuric chloride 12.5 p. of taurine | 9.4 p. of 2,5-diaminobenzene-sulfonic acid | 18.8 p. of diaminobenzene-sulfonic acid |
| 8 | 18.5 p. of cyanuric chloride 13.7 p. of p-aminobenzoic acid | 12.5 p. of N-(3-aminopropyl)-imidazole | 18.5 p. of cyanuric chloride 13.7 p. of p-aminobenzoic acid | 5.4 p. of p-phenylenediamine | 10.8 p. of p-phenylenediamine |

| Example | IR (KBr, cm$^{-1}$) |
|---|---|
| 3 | 3400, 3000, 1630, 1590, 1550, 1500, 1410, 1220, 1160, 1030, 1000 |
| 4 | 3400, 3000, 1630, 1590, 1550, 1490, 1410, 1220, 1160, 1030, 1000 |
| 5 | 3300, 3000, 1630, 1600, 1560, 1500, 1410, 1210, 1160, 1030, |
| 6 | 3300, 3000,               1570, 1500, 1420, 1210, 1160, 1030, |

9) For the synthesis of the compound of the formula IV having X=—NH—CH$_2$—CH$_2$—CH$_2$—N(C$_2$H$_5$)$_2$, $Y^1$=$Y^2$=—NH—CH$_2$—CH$_2$-SO$_3$H, Z=—NH—C$_6$H$_4$—NH— and m=2, 25.0 parts of taurine were added to 400 parts of a water/ice mixture which contains 0.4 part of a sulfonated fatty acid derivative and 36.9 parts of cyanuric chloride, in a stirred vessel, at 0° to 5° C., and the pH was kept at 6 to 9 by adding 0.2 normal NaOH solution. After the addition of the alkali, stirring was continued for two hours at 0° to 5° C. Thereafter, 13.0 parts of diethylaminopropylamine were added at about 40° C. and the pH was kept at 6 to 9 by adding 0.2 normal NaOH solution. After the addition of the alkali, stirring was continued for one hour at about 40° C. Thereafter, 16.2 parts of p-phenylenediamine were added at about 80° C. and the pH was kept at 6 to 9 by adding 0.2 normal NaOH solution. After the addition of the alkali, stirring was continued for about a further one hour at 80° C. and four hours at 95° C. After the reaction mixture had cooled to room temperature, the pH was adjusted to 1.5 with concentrated hydrochloric acid and the precipitate formed was filtered off and dried.

IR (KBr, cm$^{-1}$) 3400, 3000, 1750, 1630, 1500, 1430, 1210, 1160, 1030

10) Preparation of the amine salt solutions:

The dry products prepared in Examples 1 to 9 were suspended in water, and these suspensions were adjusted to a pH of 9 to 10 with amine. During this procedure, the solid substance dissolved. It was also possible to add the amine directly to the undried press cake after precipitation with acid in Examples 1 to 9, in order to prepare a clear solution.

PREPARATION EXAMPLES FOR PIGMENT PREPARATIONS

I) 50 parts of perylene-3,4,9,10-tetracarboxylic dianhydride, in the form of a moist press cake, were introduced into 1440 parts of demineralized water. After the suspension had been cooled to 0° C., 75 parts of a 40% strength aqueous monomethylamine solution were added dropwise in the course of 10 minutes. Stirring was continued for a further 15 minutes at 0° to 5° C., and a solution of 28.5 parts of anhydrous calcium chloride in 94.6 parts of demineralized water was then added in the course of 15 minutes. After stirring had been carried out for one hour at 0° to 5° C., 26.0 parts of 21% strength aqueous solution of the end product from Example 5 were added and the suspension was heated to 80° C. and stirred for 2 hours at this temperature. Thereafter, it was cooled to 50° C. and the pH was adjusted from 8 to 8.5 with 32.5 parts of concentrated formic acid. After stirring had been carried out for 20 minutes at 50° C., the pigment preparation was isolated, washed salt-free with water and dried. 54.8 parts of a preparation of C.I. Pigment Red 179 were obtained.

II) 50 parts of perylene-3,4,9,10-tetracarboxylic dianhydride, in the form of a moist press cake, were introduced into 1357 parts of demineralized water. After the suspension had been cooled to 0° C., 93 parts of a 32% strength aqueous monomethylamine solution were added dropwise in the course of 10 minutes. Stirring was carried out for a further 15 minutes at 0° to 5° C., and a solution of 28.5 parts of calcium chloride in 94.6 parts of demineralized water was then added. After stirring had been carried out for one hour at 0° to 5° C., 18.0 parts of 30% strength aqueous solution of the end product from Example 4 were added. The suspension was heated to 80° C. and was stirred for 2 hours at this temperature. Thereafter, it was cooled to 50° C. and the pH was adjusted to 8 to 8.5 with 29.9 parts of concentrated formic acid. After stirring had been continued for 30 minutes at 50° C., the pigment preparation was isolated, washed chloride-free with water and dried at 80° C. 58.8 parts of a preparation of C.I. Pigment Red 179 were obtained.

III) The procedure was analogous to Example I, except that 23.7 parts of a 22.5% strength aqueous solution of the end product from Example 6 were used instead of 26.0 parts of a 21% strength aqueous solution of the end product from Example 5. 57.0 parts of a preparation of C.I. Pigment Red 179 were obtained. The product contained 0.4% of calcium ions.

IV) The procedure was analogous to Example II, except that 9.0 parts of a 30% strength aqueous solution of the end product from Example 8 were used instead of 18.0 parts of the 30% strength aqueous solution of the end product from Example 4. 57.3 parts of a preparation of C.I. Pigment Red 179 were obtained.

V) The procedure was analogous to Example II, except that 18.0 parts of a 30% strength aqueous solution of the end product from Example 7 were used instead of 18.0 parts of 30% strength aqueous solution of the end product from Example 4. 54.1 parts of a preparation of C.I. Pigment Red 179 were obtained.

VI) 40 parts of C.I. Pigment Violet 23 (prepared according to BIOS 960,75), which still contained 20% of the salt resulting during the synthesis, were introduced into a stirred vessel in which 60 parts of 100% pure isobutanol and 2.5 parts of 98% strength formic acid had been initially taken. 80 parts of isobutanol (100%) and 240 parts of demineralized water were added dropwise in the course of 15 hours while stirring at 20° to 25° C. Thereafter, the isobutanol was distilled off azeotropically with steam up to a distillation temperature of 100° C. The distillation residue was filtered and the filter cake was washed salt-free with water. 64 parts of pigment press cake were obtained and said press cake was stirred with 250 parts of demineralized water and 96 parts of isobutanol as well as 24.0 parts of a 15% strength aqueous solution of the end product from Example 6 in an autoclave. The suspension was heated at 125° C. for 3 hours. It was allowed to cool to 80° C., and the isobutanol was distilled off azeotropically with steam up to a distillation temperature of 100° C. The distillation residue was filtered and the filter cake was washed with water and dried at 80° C. 32 parts of a preparation of C.I. Pigment Violet 23 were obtained.

VII) 31.0 parts of C.I. Pigment Violet 23, which was prepared according to BIOS 960,75, were introduced as a moist press cake (40% strength) into 96 parts of isobutanol (100%) and 195 parts of demineralized water. 2.5 parts of concentrated formic acid and 11.0 parts of NaCl were added, and the mixture was refluxed for 1 hour. It was allowed to cool to 60° C., and the pH was adjusted to 8 to 9 with dilute sodium hydroxide solution. Thereafter, 20.7 parts of a 15% strength aqueous solution of the end product from Example 4 were added, the mixture was stirred for 30 minutes and the isobutanol was distilled off azeotropically with steam up to a distillation temperature of 100° C. The distillation residue was filtered and the filter cake was washed chloride-free with water and dried at 80° C. 31.4 parts of a preparation of C.I. Pigment Violet 23 were obtained.

VIII) 30.0 parts of C.I. Pigment Violet 23, in the form of a moist press cake (solids content 40%), were introduced into 95 parts of isobutanol (100%) and 195 parts of demineralized water, and stirring was carried out for 1 hour to give a homogeneous mixture. 13.7 parts of a 27% strength aqueous solution of the end product from Example 6 were added and the mixture was heated to the reflux temperature and refluxed for 1 hour. Thereafter, the isobutanol was distilled off with steam. The distillation residue was filtered and the filter cake was washed with water and dried at 80° C. 30.5 parts of a preparation of C.I. Pigment Violet 23 were obtained.

IX) 30 parts of C.I. Pigment Violet 23 in the form of a moist press cake (solids content 40%), were introduced into 280 parts of demineralized water and stirred for 15 minutes to give a homogeneous mixture. The latter was heated to 90° to 95° C., 13.3 parts of a 23% strength aqueous solution of the end product from Example 7 were added and the mixture was allowed to cool to 30° C. while stirring. After filtration and drying at 80° C., 29.5 parts of a preparation of C.I. Pigment Violet 23 were obtained.

X) 44 parts of 2,9-dimethylquinacridone (C.I. Pigment Red 122), in the form of a moist press cake (content 24.5%), were introduced into a stirred vessel in which 270 parts of isobutanol (100%), 2.5 parts of sodium hydroxide and 50 parts of demineralized water had been initially taken. The suspension was stirred for 15 hours at about 20° C. and then heated at 125° C. for 3 hours in an autoclave. The isobutanol was then removed by steam distillation, and 25.1 parts of a 17.5% strength aqueous solution of the end product from Example 3 were added at 50° C. to the aqueous suspension. Stirring was continued for a further 3 hours at 20° to 25° C. Thereafter, the mixture was filtered and the filter cake was washed with water and dried at 80° C. 43.4 parts of a preparation of C.I. Pigment Red 122 were obtained.

XI) The procedure was as described in Example VIII, except that the pigment preparation was isolated by spray drying instead of by filtration. 23 parts of a preparation of C.I. Pigment Violet 23 were obtained.

XII) 23 parts of a copper phthalocyanine (C.I. Pigment Blue 15), in the form of a moist press cake (solids content 23.5%), were introduced into 250 parts of demineralized water and stirred overnight to give a homogeneous mixture. The latter was then heated to 80° C.

and adjusted to pH 9 to 9.5 with dimethylethanolamine, and 10.2 parts of a 22% strength aqueous solution of the end product from Example 6 were added. Stirring was continued for a further 30 minutes, the mixture being allowed to cool to room temperature. Thereafter, the mixture was filtered, and the filter cake was then washed with water and dried at 80° C. 23.3 parts of a preparation of C.I. Pigment Blue 15 were obtained.

USE EXAMPLES FOR PIGMENT DISPERSIONS

A) 70 parts of a milled dolomite were dispersed in 30 parts of a 22.6% strength aqueous solution of the end product from Example 6 in a dissolver for 45 minutes. The addition of 6 parts of demineralized water gave a low-viscosity dispersion whose rheology was rated at mark 4, whereas the rheology of a paste obtained without the end product from Example 6 was rated as completely set (mark 1).

B) 8.0 parts of a gas black which had been aftertreated by oxidation, had a BET specific surface area of 470 m$^2$/g and had a pH of 2.5 in aqueous suspension were dispersed in 71.2 parts of demineralized water by means of a dissolver for 60 minutes, with the addition of 1.8 parts of a 22% strength aqueous solution of the end product from Example 4. A free-flowing dispersion whose rheology was rated at 4 was obtained, whereas a slightly set dispersion (mark 2) resulted when the compound according to the invention was omitted.

C) 5.0 parts of the same gas black as in Example B, which had been aftertreated by oxidation, were dispersed in 42.5 parts of a 16% strength aqueous polyurethane dispersion in the presence of 50 parts of glass beads (diameter 1.0 mm) in a dissolver for 60 minutes, with the addition of 2.2 parts of an aqueous solution of the end product from Example 6 and 0.5 part of a commercial antifoam. A free-flowing, stable dispersion whose rheology was rated at 4 was obtained.

D) 41.5 parts of demineralized water were added to 50.0 parts of a 40% strength moist press cake of C.I. Pigment Violet 23, with the addition of 8.5 parts of a 22% strength aqueous solution of the end product from Example 6. 100 parts of glass beads (diameter 1.0 mm) were added and dispersing was carried out for 60 minutes in a laboratory bead mill. After the beads had been removed by sieving, a free-flowing dispersion of C.I. Pigment Violet 23, whose rheology was rated at 5, was obtained.

E) 6.0 parts of dimethylperylimide (C.I. Pigment Red 179), 53.4 parts of a 16% strength aqueous polyurethane dispersion and 0.6 part of a commercial antifoam were homogenized together with 2.8 parts of a 22% strength aqueous solution of the end product from Example 6 in a dissolver for 15 minutes. After the addition of 100 parts of glass beads (diameter 1.0 mm), dispersing was carried out for 60 minutes in a laboratory bead mill at 40° C. A free-flowing paste (rheology 5) was obtained which, after dilution ("thinning") with 119.2 parts of an 18% strength aqueous polyurethane resin and 20.8 parts of demineralized water, gave a markedly more intense coating compared with a pigment (comparison) which was dispersed without the addition of the substance according to the invention.

|  | FS 3% P | 1:10 TiO$_2$ | 50:50 Met | Visc(s) |
|---|---|---|---|---|
| Comparison | — | — | — | 2.5 |
| Example E | very little more transparency | significantly more intense | distinctly more intense | 1.0 |

-continued

|  | FS 3% P | 1:10 TiO$_2$ | 50:50 Met | Visc(s) |
|---|---|---|---|---|
| parent |  |  |  |  |

F) 12.0 parts of C.I. Pigment Violet 23, 47.5 parts of a 25% strength aqueous polyurethane resin and 0.5 part of a commercial antifoam were stirred for 15 minutes in a dissolver, after the addition of 5.5 parts of a 22% strength aqueous solution of the end product from Example 6, until a homogeneous mixture was obtained, and then, after the addition of 90 parts of glass beads (diameter 1.0 mm), were milled for 60 minutes in a mini-sand mill. After the beads had been removed by sieving, thinning was effected with 330.1 parts of a 15.3% strength aqueous polyurethane dispersion and 9.9 parts of demineralized water. A distinctly more intense and more glossy coating was obtained with this coating material compared with a paste without the compound according to the invention (comparison).

|  | FS 3% P | 1:10 TiO$_2$ | 50:50 Met | Gloss |
|---|---|---|---|---|
| Comparison | — | — | — | 15 |
| Example F | identical transparency | significantly more intense | significantly more intense | 56 |

G) 20.0 parts of the pigment preparation of C.I. Pigment Red 179 from Example II, 44.0 parts of demineralized water and 36.0 parts of a 27% strength aqueous polyacrylate resin were homogenized for 15 minutes by means of a dissolver. After the addition of 660 parts of zirconium dioxide beads (diameter 1.0 to 1.6 mm) and a further 33.3 parts of demineralized water, this suspension was dispersed for 90 minutes in a 0.5 l laboratory bead mill. A 15% strength pigment paste having very good flow properties and a long shelf life was obtained. This paste was diluted with an aqueous polyurethane dispersion to a pigment content of 5%, and a markedly more intense and more transparent coating was obtained therewith in comparison to a pigment which was prepared according to U.S. Pat. No. 4,496,731, Example 5.

H) 6.0 parts of the pigment preparation of C.I. Pigment Red 179 from Example III, 0.5 part of a commercial antifoam and 53.5 parts of a 30% strength aqueous polyester dispersion were premixed for 15 minutes with a dissolver and, after the addition of 100 parts of glass beads (diameter 1.0 mm), dispersed for 60 minutes in a mini-sand mill at 50° C. A 10% strength pigment paste having good flow properties was obtained. This paste was thinned with 90 parts of a 26% strength aqueous polyester/melamine resin dispersion to a pigment content of 3%, and a markedly more intense and more transparent coating was obtained therewith compared to a pigment prepared according to U.S. Pat. No. 4,496,731.

J) 6.0 parts of the preparation of C.I. Pigment Red 179 from Example III, 53.4 parts of a 16% strength aqueous polyurethane dispersion and 0.6 part of a commercial antifoam were homogenized for 15 minutes in a dissolver. After the addition of 100 parts of glass beads (diameter 1.0 mm), dispersion was carried out for 60 minutes in a mini-sand mill at 40° C. A paste was obtained which had better flow properties compared with a commercial pigment and, after thinning with 119.2 parts of an 18% strength aqueous polyurethane resin and 20.8 parts of demineralized water, gave a distinctly more transparent and more intense coating compared with pigments which were prepared according to U.S. Pat. No. 4,496,731 or U.S. Pat. No. 4,189,582, and with pigment preparations containing additives, as described in U.S. Pat. No. 3,622,339, Example 5, and U.S. Pat. No. 4,314,001, Example 3.

Flow curves were recorded using a rotary viscometer (conditions: 22° C., stationary for 10 minutes, increase to maximum rotational frequency in 2 minutes, maintaining for 1 minute and decreasing the rotational frequency to zero in 2 minutes) in order to compare the rheological behavior of the pigment preparation according to the invention from Example J with that of a pigment which was prepared according to U.S. Pat. No. 4,496,731, Example 5. The pigment preparation according to the invention showed a decrease in viscosity of about 25% relative to the comparison.

The coloristic test gave the following differences:

|  | FS 3% P | 1:10 TiO$_2$ | 50:50 Met | Gloss |
|---|---|---|---|---|
| Pigment with additive according to U.S. Pat. No. 4,314,001 Example J | — significantly more transparent FS 3% P | — significantly more intense 1:10 TiO$_2$ | — significantly more intense 50:50 Met | 22 61 |
| Pigment according to U.S. Pat. No. 4,496,731 (Example 5) Example J | — significantly more transparent FS 3% P | — distinctly more intense 1:10 TiO$_2$ | — distinctly more intense 50:50 Met | |
| Pigment according to U.S. Pat. No. 4,189,582 (Example 2) Example J | — distinctly more transparent | — markedly more intense | — very little more intense | |

Comparison of the hue angles (measured according to DIN 5033) of different pigment preparations gave the following values: pigment preparation containing the compound according to the invention from Example J: 27.5 degrees, pigment preparation according to U.S. Pat. No. 4,189,582, Example 2: 23 degrees, pigment preparation according to U.S. Pat. No. 4,496,731, Example 5: 21 degrees.

K) 12.0 parts of the pigment preparation of C.I. Pigment Violet 23 from Example VII, 0.5 part of a commercial antifoam and 47.5 parts of a 20% aqueous polyurethane resin solution were dispersed for 60 minutes in a mini-sand mill at 40° C. after the addition of 100 parts of glass beads (diameter 1.0 mm). A 20% strength pigment paste having very good flow properties was obtained. This paste was thinned with 330.1 parts of a 15.3% strength aqueous polyurethane dispersion and 9.9 parts of demineralized water to a pigment content of 3%, and a significantly more transparent and more intense coating having higher glass was obtained therewith compared to an untreated pigment (comparison) and a pigment which was prepared according to U.S. Pat. No. 4,253,839, Example 2.

|  | FS 3% P | 1:10 TiO$_2$ | 50:50 Met | Visc(s) | Gloss |
|---|---|---|---|---|---|
| Comparison | — | — | — | 3.5 | 30 |
| Example K | significantly more transparent FS 3% P | considerably more intense 1:10 TiO$_2$ | considerably more intense 50:50 Met | 4.9 Visc(s) | 71 Gloss |
| Pigment according to U.S. Pat. No. 4,253,839 Example K | — distinctly more transparent | — considerably more intense | — significantly more intense | 8.9 4.9 | 30 71 |

Formulae

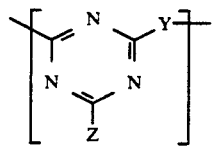

I

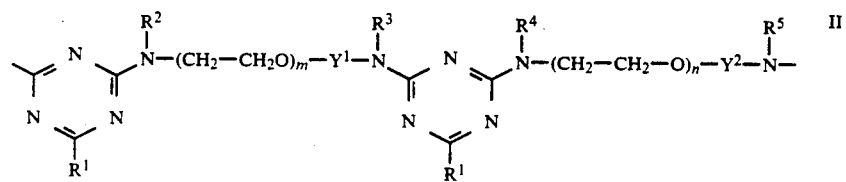

II

Formulae
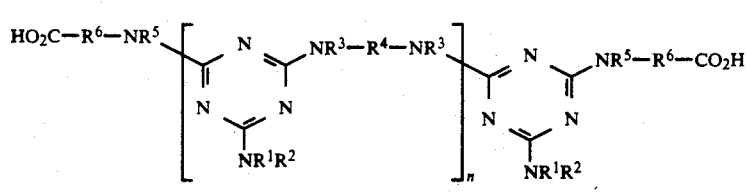
III
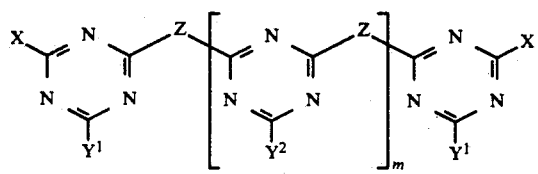
IV
Reaction schemes
1) 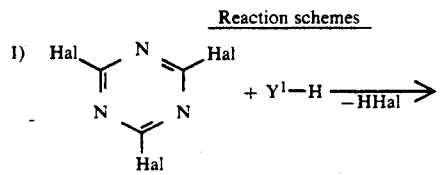 + Y¹—H $\xrightarrow{-HHal}$
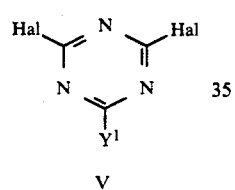
V
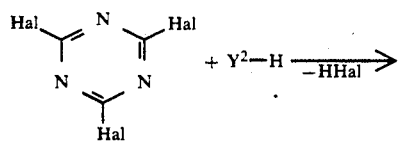 + Y²—H $\xrightarrow{-HHal}$
VI
2) 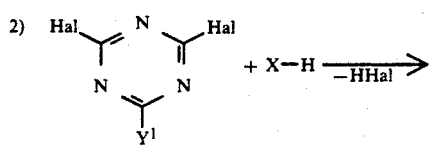 + X—H $\xrightarrow{-HHal}$
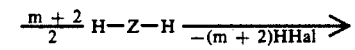
VII
-continued
Reaction schemes
2 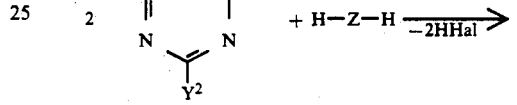 + H—Z—H $\xrightarrow{-2HHal}$
VI
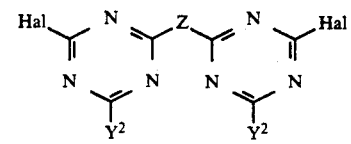
VIII
3) 2 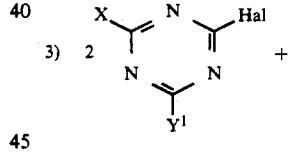 +
VII
$\frac{m}{2}$ 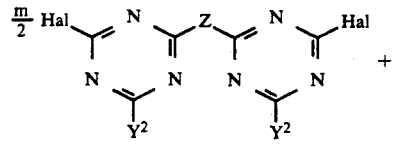 +
VIII
$\frac{m+2}{2}$ H—Z—H $\xrightarrow{-(m+2)HHal}$
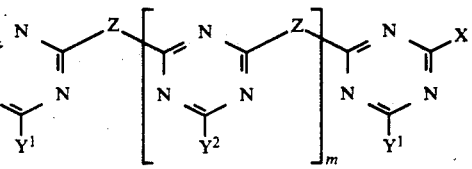
IV
We claim:
1. A triazine compound of formula IV

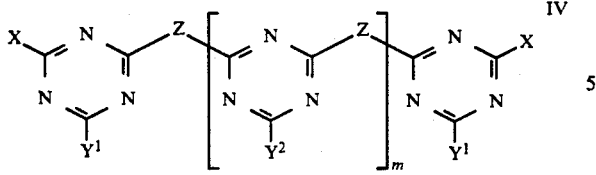

wherein
X is a group of the formula IVa $$-A^1-D^1-NR^1R^2 \qquad \text{IVa}$$

in which $A^1$ is a bridge member selected from the group consisting of O, S or $NR^3$, wherein $R^3$ is hydrogen or a $C_1$–$C_{22}$-alkyl radical or a $C_3$–$C_{22}$-alkenyl radical which is unsubstituted or substituted by an OH group, $D^1$ is an phenylene or benzylene group or a branched or straight-chain $C_2$–$C_{12}$-alkylene group which may be interrupted by one or more bridge members selected from the group $A^2$, and $A^2$, independently of $A^1$, is selected from the same group of substituents as $A^1$, and $R^1$ and $R^2$, independently of one another, are branched or straight-chain $C_1$–$C_{20}$-alkyl groups of $C_3$–$C_{20}$-alkenyl groups, or in which $R^1$ and $R^2$, together with the nitrogen atom, form an unsaturated or saturated five- or six-membered ring which optionally contains one or two nitrogen, atoms as further hetero atoms in the ring, or wherein X is a group of the formula IVb

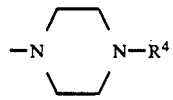

in which $R^4$ is $C_1$–$C_6$-alkyl, and
$Y^1$ and $Y^2$, independently of one another are each a group of the formula IVc $$-A^3-D^2-E^1 \qquad \text{IVc}$$

in which $A^3$ is independent of $A^1$ and is a bridge member selected from the same group of substituents as $A^1$, $D^2$ is independent of $D^1$ and is selected from the same group of substituents as $D^1$ or is $CH_2$ or a direct bond, and $E^1$ is an anion-forming group, selected from the groups COOM, $SO_3M$, $OSO_3M$ or $OPO_3M_2$, wherein M is hydrogen, a metal, or an ammonium ion which is unsubstituted or substituted by aliphatic, aromatic or araliphatic radicals, and Z is a group of the formula IVd $$-A^4-Z^*-A^4- \qquad \text{IVd}$$

in which $A^4$ is independent of $A^1$ and is a bridge member selected from the same group of substituents as $A^1$ and $Z^*$ is the group CO, branched or straight-chain $C_2$–$C_{25}$-alkylene, $C_5$–$C_6$-cycloalkylene or $C_6$–$C_{14}$-arylene which is unsubstituted or substituted by COOM, $SO_3M$, Cl, OH or alkoxy groups, in which M has the abovementioned meanings, and wherein, in the cyclic compounds, some of the carbon atoms are optionally replaced by the hetero atoms nitrogen, or wherein $Z^*$ is a group of the formula (IV-d')-$C_2$–$C_3$ alkylene -$Z^{}$-$C_2$–$C_3$-alkylene in which $Z^{}$ is the group N-$C_1$–$C_{20}$-alkyl, NH or O, or wherein Z is a bridge member of the formulae IVe and IVf $$-NH-C_6H_4-A^5-C_6H_4-NH- \qquad \text{IVe}$$

$$-NH-C_2-C_3\text{-alkylene}-A^5-C_2-C_3\text{-alkylene}-NH- \qquad \text{IFV}$$

in which $A^5$ is a group of the formula $CR^5R^6$, $NR^7$, O, SO, $SO_2$ or CO, in which $R^5$ and $R^6$, independently of one another may be branched or straight-chain $C_1$–$C_4$-alkyl groups or hydrogen and wherein $R^7$, independently of $R^3$, is selected from the same group of substituents as $R^3$, or Z is any combination of the groups of the formulae IVd, IVe and IVf, and m is an integer from 1 to 100.

2. A triazine compound of the formula IV as claimed in claim 1, wherein

X is a group of the formula IVa $$-A^1-D^1-NR^1R^2 \qquad \text{IVa}$$

in which $A^1$ is a bridge member selected from the group consisting of O or $NR^3$, wherein $R^3$ is hydrogen or a $C_1$–$C_{22}$-alkyl radical or a $C_3$–$C_{22}$-alkyl radical which is unsubstituted or substituted by an OH group, $D^1$ is an phenylene or benzylene group or a branched or straight-chain $C_2$–$C_{12}$-alkylene group which are optionally interrupted by one or more bridge members selected from the group $A^2$, and $A^2$, independently of $A^1$, is selected from the same group of substituents as $A^1$, and $R^1$ and $R^2$, independently of one another, are branched or straight-chain $C_1$–$C_{20}$-alkyl groups of $C_3$–$C_{20}$-alkenyl groups, or in which $R^1$ and $R^2$, together with the nitrogen atom, form an unsaturated or saturated five- or six-membered ring which may additionally contain one or two nitrogen atoms as further hetero atoms in the ring, or wherein X is a group of the formula IVb

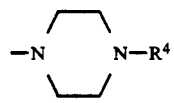

in which $R^4$ is $C_1$–$C_6$-alkyl, and
$Y^1$ and $Y^2$, independently of one another are each a group of the formula IVc $$-A^3-D^2-E^1 \qquad \text{IVc}$$

in which $A^3$ is independently of $A^1$ and is a bridge member selected from the same group of substituents as $A^1$, $D^2$ is independent of $D^1$ and is selected from the same group of substituents as $D^1$ of is $CH_2$ or a direct bond, and $E^1$ is an anion-forming group, selected from the groups COOM or $SO_3M$, wherein M is hydrogen, a metal, or an ammonium ion which is unsubstituted or substituted by aliphatic, aromatic and araliphatic radicals, and Z is a group of the formula IVd $$-A^4-Z^*-A^4- \qquad \text{IVd}$$

in which $A^4$ is independent of $A^1$ and is a bridge member selected from the same group of substituents as $A^1$ and $Z^*$ is the group CO, $NR^3$, in which $R^3$ has the abovementioned meaning, branched or straight-chain $C_2$–$C_{25}$-alkylene, $C_5$–$C_6$-cycloalkylene or phenylene, which is unsubstituted or substituted by COOM or $SO_3M$, in which M has the abovementioned meanings, and wherein, in the cyclic compounds, some of the carbon atoms may be replaced by the hetero atoms nitrogen, or Z is a combination of the groups of the formula IVd, and m is an integer of 1 to 100.

3. A triazine compound of the formula IV as claimed in claim 1, wherein

X is a group of the formula IVg ps ti $-A^1-D^1-NR^1R^2$  IVg wherein $A^1$ is $NR^3$, in which $R^3$ is methyl or hydrogen, $D^1$ is a branched or straight-chain $C_2$–$C_6$-alkylene group or a phenylene group and $R^1$ and $R^2$, independently of one another are branched or straight chain $C_1$–$C_6$ alkyl groups, or in which $R^1$ and $R^2$, together with the nitrogen atom, form an unsaturated or saturated five- or six-membered ring which may additionally contain one or two nitrogen atoms as further hetero atoms in the ring, and $Y^1$ and $Y^2$, independently of one another are each a group of the formula IVh $$A^3-D^2-E^1 \qquad \text{IVh}$$

wherein $A^3$ is $NR^3$, in which $R^3$ is methyl or hydrogen and $D^2$ is independent of $D^1$ and is selected from the same group of substituents as $D^1$ or is $CH_2$ or a direct bond, and $E^1$ is an anion-forming group selected from the groups COOM or $SO_3M$, wherein M is hydrogen, a metal or an ammonium ion which is unsubstituted or substituted by aliphatic, aromatic and araliphatic radicals, and Z is a group of the formula
$-A^4-Z^*-A^4$, wherein $A^4$ is $NR^3$, in which $R^3$ is methyl or hydrogen and $Z^*$ is the group $C_2$–$C_6$-alkylene or phenylene, which is unsubstituted or substituted by COOM or $SO_3M$, in which M has the abovementioned meanings, or wherein $Z^*$ is a group of the IVi.

$$-C_2-C_3\text{-alkylene-}Z^{**}-C_2-C_3\text{-alkylene} \qquad \text{IVi}$$

in which $Z^{**}$ is the group $N-C_1$–$C_{20}$-alkyl, NH or O, and m is an integer of from 1 to 30.

4. A triazine compound of the formula IV as claimed in claim 1, wherein M is an alkali metal or the stoichiometric amount of an alkaline earth metal.

5. Method of using a compound as claimed in claim 1 as pigments.

* * * * *

UNITED STATES PATENT AND TRADEMARK OFFICE
CERTIFICATE OF CORRECTION

PATENT NO.   : 5,240,499
DATED        : Aug. 31, 1993
INVENTOR(S)  : Rainer Az, et al It is certified that error appears in the above-indentified patent and that said Letters Patent is hereby corrected as shown below:

In claim 1, column 19, line 27, "of" should read --or--.

In claim 1, column 20, line 10, "IFV" should read --IVf--.

In claim 2, column 20, line 30, the phrase "$C_3$-$C_{22}$-alkyl" should read --$C_3$-$C_{22}$-alkenyl--.

In claim 2, column 20, line 40, the phrase "groups of" should read --group or--.

In claim 2, column 20, line 63, the phrase "as $D^1$ of is" should read --as $D^1$ or is--.

In claim 3, column 21, line 20, the phrase "ps ti" should be deleted

Signed and Sealed this

Third Day of May, 1994

Attest:

BRUCE LEHMAN

*Attesting Officer*     *Commissioner of Patents and Trademarks*